United States Patent [19]

Covey et al.

[11] Patent Number: 4,874,891
[45] Date of Patent: Oct. 17, 1989

[54] OPEN "D" RING HORMONE ANALOGS

[75] Inventors: Douglas F. Covey; Ricahrd J. Auchus, both of St. Louis, Mo.

[73] Assignee: Washington University, St. Louis, Mo.

[21] Appl. No.: 858,393

[22] Filed: May 1, 1986

[51] Int. Cl.[4] .............................................. C07C 67/02
[52] U.S. Cl. ..................... 560/256; 560/255; 560/5; 562/403; 568/326; 568/373; 568/439; 568/445; 568/633; 568/665; 568/714
[58] Field of Search ........................ 560/255, 256, 5; 549/544; 568/439, 445, 714, 326, 373, 633, 665; 562/403

[56] References Cited

U.S. PATENT DOCUMENTS

| | | | |
|---|---|---|---|
| 2,534,486 | 12/1950 | Ambrose et al. | 178/5.2 |
| 2,542,936 | 2/1951 | Miescher et al. | 560/5 |
| 3,192,257 | 6/1965 | Zderic | 260/514.5 |
| 3,275,691 | 9/1966 | Goldberg et al. | 568/714 |
| 3,309,383 | 3/1967 | Pappo | 260/343.3 |
| 3,314,971 | 4/1967 | Goldberg et al. | 260/326.5 |
| 3,478,083 | 11/1969 | Freiberg | 568/373 |
| 3,483,226 | 12/1969 | Baran | 260/345.2 |
| 3,681,427 | 8/1972 | Edwards et al. | 560/5 |
| 3,839,420 | 10/1974 | Crabbe et al. | 560/257 |
| 3,880,889 | 4/1975 | Edwards et al. | 560/5 |
| 4,322,416 | 3/1982 | Metcalf et al. | 424/242 |

OTHER PUBLICATIONS

Thomas, J. L., et al, *J Biol Chem* (1983) 258: 11500-11504.
Tobias, B., et al, *J Biol Chem* (1982) 257: 2783-2786.
Johnston, J. O. et al, *Novel Approaches to Cancer Chemotherapy* Sunkara, P. S., ed. (1984) Academic Press, pp. 307-358.
Zimniski, S. J., et al, *Eigth Annual San Antonio Breast Cancer Symposium* (1985) Abstract No. 83.
Brandt M. E., et al, *Endocrine Society Symposium* (1985) Abstract No. 761.

*Primary Examiner*—Paul J. Killos
*Attorney, Agent, or Firm*—Irell & Manella

[57] ABSTRACT

Compounds of the formula:

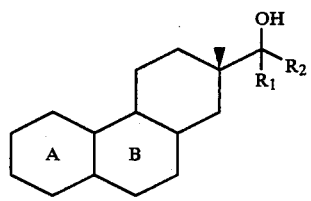

and the pharmaceutically acceptable esters thereof, wherein rings A and B are selected from the group consisting of

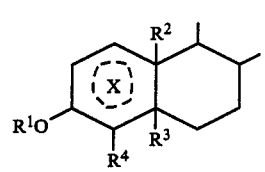

(a)

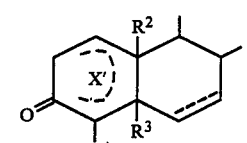

(b)

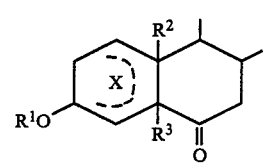

(c)

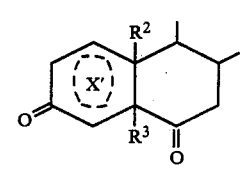

(d)

wherein $\overset{\frown}{x}$ represents an aromatic ring, or the presence or absence of 0, 1, or 2 conjugated or unconjugated $\pi$ bond(s), and
wherein $\overset{\frown}{x'}$ represents the presence or absence of 0, 1, or 2 conjugated or unconjugated $\pi$ bond(s), and
wherein a non-aromatic $\pi$ bond, if present, may optionally be converted to an epoxide;
and wherein the dotted line represents the presence or absence of a $\pi$ bond,
and wherein:
$R^1$ is H, acyl(1-6), or alkyl(1-6);
$R^2$ is H, alkyl(1 $\propto$ 6), 2-propynyl, or allenyl;
$R^3$ and $R^4$ is each independently H or $OR^5$, wherein $R^5$ is H, acyl(1-6), or alkyl(1-6); and
wherein $R_1$ and $R_2$ is each independently H, alkyl(-1-6) or is —C≡CR$_3$, —CH=CHR$_3$, or —CH=C=CHR$_3$, wherein $R_3$ is selected from the group consisting of H, halo, $CF_3$, alkyl(1-6), acyloxy, carboxylate, carboalkoxylate, alkoxy, or alkylthio;
and wherein when at least one of $R_1$ and $R_2$ is H, the compound of Formula 1 may also be in the oxidized oxo form and when both $R_1$ and $R_2$ are H, the compound of Formula 1 may also be in the oxidized carboxylic acid form or the alkyl(1-6) ester thereof are useful in regulating steroid metabolism.

11 Claims, No Drawings

OPEN "D" RING HORMONE ANALOGS

TECHNICAL FIELD

The invention relates to regulation of steroid hormone metabolism. More specifically, the invention concerns steroid hormone analogs having open "D" rings which influence steroid hormone metabolism and balance.

BACKGROUND ART

Regulation, biological effect, internal relationship, and control of steroid sex hormone synthesis and activity are complex and incompletely understood. However, the basics of this regulatory system are clear. It is known, for example, that the androgenic members of this class have nonaromatic "A" rings in the steroid nucleus, whereas the estrogens, as a group, contain aromatic "A" rings. It is also known that these hormones regulate cellular metabolism by binding to specific receptor sites in target cells. This observation has been of considerable importance in therapy for tumors related to sexually differentiated tissues. Depending on the presence or absence of the appropriate receptor, these tumors may or may not respond to therapy consisting in withdrawal of, or supply of, sex hormones. This treatment may be surgical, such as removal of the ovary to deplete the supply of estrogens, or medical such as by administration of the hormones or of their agonists or inhibitors.

Therapeutic surgery or administration of sex hormone medicaments is not limited to tumor treatment. Other metabolic processes are also related to these hormone levels. For example, it is now clear that the estrogen level influences considerably the mechanisms which regulate the formation or resorption of bone, and estrogen therapy has become conventional in the treatment of osteoporosis.

Thus, in a manner analogous to, for example, analgesia, compounds which influence the pathways regulating steroid sex hormone levels and activities have important therapeutic uses in a variety of contexts even though the mechanisms whereby they alter the hormone pattern are poorly defined. For example, $10\beta$-propynyl-substituted steroids, a class of inhibitors for aromatase ( an enzyme responsible for conversion of the nonaromatic androgens into the corresponding aromatized estrogens) has been found useful in treatment of hormone-dependent breast and endometrial cancers. These compounds have been shown to be suicide inhibitors of aromatase in vitro and have been shown to cause mammary tumor regression in vivo in rats. (See U.S. Pat. No. 4,322,416; Covey, D. F., et al, *J Biol Chem* (1981) 256:1076–1079 Johnston, J. O., et al, in *Novel Approaches to Cancer Chemotherapy*) Sunkara, P. S., ed (1984) Academic Press, pp. 307–358; Zimniski, S. J., et al. *Eighth Annual San Antonio Breast Cancer Symposium* (1985), Abstract No. 83: Brandt, M. E., et al, *Endocrine Society Symposium* (1985), Abstract No. 761.)

An additional enzyme significant in regulation of circulating and intracellular steroid hormone metabolism is the enzyme estradiol dehydrogenase (EC 1.1.1.62), otherwise called $17\beta,20\alpha$-hydroxysteroid dehydrogenase ($17\beta$-HSD). This enzyme in human placenta is a dimer of molecular weight 68 kd which catalyzes the interconversion of estrone and $17\beta$-estradiol using either NAD+/NADH or NADP+/NADPH as cofactors. It also catalyzes the conversion of $16\alpha$-hydroxyestrone to estriol. (Estriol production is considerably amplified during pregnancy, and since $17\beta$-HSD has been purified from the placenta, it is thought that formation of estroil may be its chief metabolic function.) Placental and other $17\beta$-HSD enzymes interconvert androstenedione and testosterone.

Diagram 1 summarizes the interrelationships of the steroid hormones whose levels are best known to be regulated by aromatase and $17\beta$-HSD.

Diagram 1

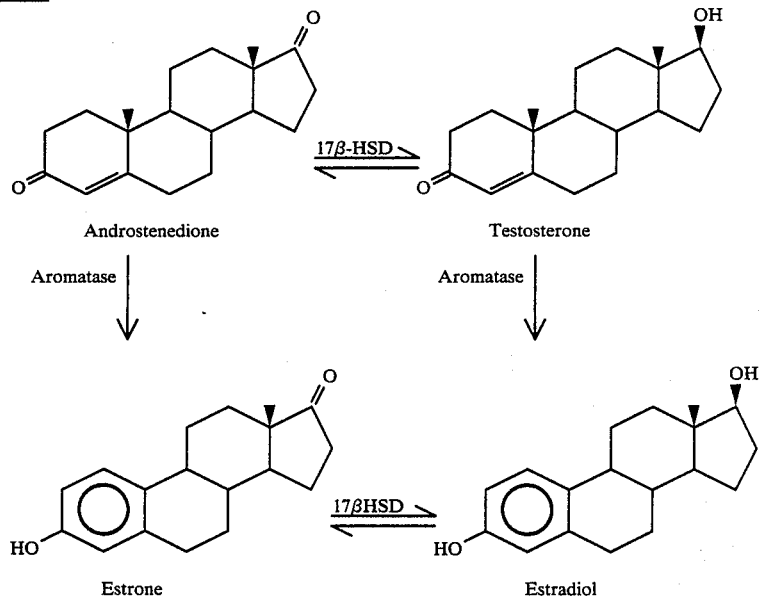

Androstenedione    Testosterone

Estrone    Estradiol

Referring to Diagram 1, both estradiol and testosterone have more potent activities with respect to estrogenicity and androgenicity, respectively, than their corresponding oxidized forms estrone and androstenedione. Therefore regulation of $17\beta$-HSD results in regulation of the effective level of steroid sex hormones. In premenopausal women, aromatase is effective in the ovary in converting both androstenedione and testosterone to their respective aromatized forms and estradiol production from testosterone is, therefore, independent of the activity of 17β-HSD (for a given level of testosterone). On the other hand, in postmenopausal women, most estrogen synthesis is extraglandular and is by conversion of androstenedione to estrone. This form of estrogen biosynthesis has been shown in a wide variety of tissues, and effective estrogen levels depend on the ability of 17β-HSD to convert the estrone to estradiol.

The conventional steroid numbering system is used in the following discussion and hereinbelow, unless otherwise specified. This system is shown under the Definitions section below.

Because the aromatization of the "A" ring utilizes a mechanism which involves oxidation at C-19 of the steroid system, compounds containing modifications proximal to this carbon have been studied with respect to impacting aromatase activity. On the other hand, the oxidation catalyzed by 17β-HSD is at C-17, which carbon is a member of the "D" ring. In analogy to the approach taken with respect to aromatase, potential suicide inhibitors of 17β-HSD have been suggested which contain modifications proximal to C-17, including modification at C-16 by substitution with a methylene group (Thomas, J. L., et al, *J Biol Chem* (1983) 258:11500–11504) and by utilizing a 20α-acetylene substitution (Tobias, B., et al, *J Biol Chem* (1982) 257:2783–2786). These inhibitors have been characterized in terms of their binding affinity (Km) their turnover number (Vmax) and by their partition ratio ($R_p$). Each compound has a particular pattern of these variables; no single pattern is necessarily ideal for every metabolic condition.

It has now been found that an additional class of compounds capable of influencing steroid sex hormone metabolism is characterized by an open "D" ring to provide a hydroxymethyl or α-oxo substituent to the steriod "C" ring, which substituent can be further substituted either to provide suicide inhibition capacity, or to serve as a direct inhibitor of the enzyme or as an inhibitor to binding of the normally produced sex hormones to the appropriate receptor. Both male and female hormone analogs are useful in this way; the oxidation state of the "A" ring may or may not be significant with respect to the capacity of these compounds to perform a regulatory function according to a particular mechanisms. Accordingly, the compounds of the invention add to the repertoire of available therapeutic tools in treatment of conditions requiring regulation of hormone metabolism.

DISCLOSURE OF THE INVENTION

The invention provides a group of compounds which have in common the conventional variations of A, B and C rings found in the steroid nucleus and an opened D ring. The D ring is replaced by a derivatized hydroxymethyl or α-oxo substituent at position 13 of the steroid system, thus providing a modified 3-ring carbocyclic nucleus. The substituent at C-13 (using the steroid numbering system) either provides a center for suicide inhibition, general competitive inhibition of the target 17β-HSD enzyme, or inhibition of binding of the various sex hormones to receptors.

Thus in one aspect, the invention is directed to a compound of the formula:

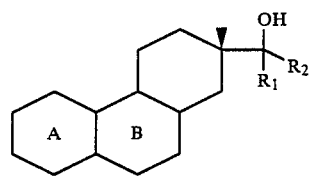
(1)

and the pharmaceutically acceptable esters thereof, wherein rings A and B are selected from the group consisting of

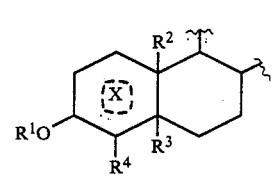
(a)

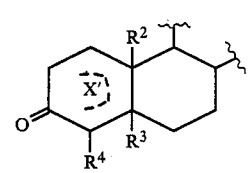
(b)

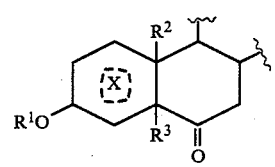
(c)

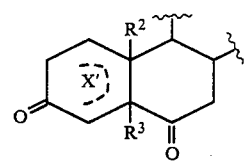
(d)

wherein $\{\overline{x}\}$ represents an aromatic ring, or the presence or absence of 0, 1, or 2 conjugated or unconjugated π bond(s), and wherein $\overline{x}$ represents the presence or absence of 0, 1, or 2 conjugated or unconjugated π bond(s), and wherein a non-aromatic π bond, if present, may optionally be converted to an epoxide;

and wherein the dotted line ------ represents the presence or absence of a π bond, and wherein:

$R^1$ is H, acyl(1–6), or alkyl(1–6);

$R^2$ is H, alkyl(1–6), 2-propynyl, or allenyl;

$R^3$ and $R^4$ is each independently H or $OR^5$, wherein $R^5$ is H, acyl(1–6), or alkyl(1–6); and wherein $R_1$ and $R_2$ is each independently H, alkyl(1–6) or is —C≡CR₃, —CH=CHR₃, or —CH=C=CHR₃, wherein $R_3$ is selected from the group consisting of H, halo, CR₃, alkyl(1–6), acyloxy, carboxylate, carboalkoxylate, alkoxy, or alkylthio;

and wherein when at least one of $R_1$ and $R_2$ is H, the compound of Formula 1 may also be in the oxidized oxo form and when both $R_1$ and $R_2$ are H, the compound of Formula 1 may also be in the oxidized carboxylic acid form or the alkyl(1-6) ester thereof.

(It is of course understood that $R^2$ and $R^3$ can be as stated only for those embodiments which permit the valence required at C-10 or C-5; where C-10 or C-5 is a part of a $\pi$ bond, $R^2$ or $R^3$, respectively, is not present. It is further understood that only non-aromatic $\pi$ bonds are optionally in the form of the epoxide.)

The compounds of the invention are inhibitors of either or both 17-HSD enzymes involved in androgen or estrogen hormone metabolism. Embodiments wherein the A ring is aromatic are generally more effective with that which catalyzes the interconversion of estrone and estradiol; these wherein the A ring is nonaromatic affect the androstenedione/testosterone interconversion more strongly.

In other aspects, the invention is directed to pharmaceutical compositions containing the compounds of Formula 1 and to methods of treating hormonal imbalances and to treating other conditions responsive to hormonal regulation by administration of the compounds of Formula 1 or their compositions. In still other aspects the invention relates to methods to prepare the compounds of Formula 1 and to intermediates in their preparation.

MODES OF CARRYING OUT THE INVENTION

A. Definitions

As used herein "alkyl" refers to a branched or unbranched saturated hydrocarbon chain containing 1-6 carbon atoms such as methyl, ethyl, propyl, tert-butyl, n-hexyl, and 3-methyl-n-butyl.

"Alkoxy", "alkylthio", and "acyl" refer to the groups —OR, —SR, and —COR, respectively wherein R is alkyl as above defined.

"Propynyl" refers to the group —CH$_2$—C≡CH, and "allenyl" refers to the group —CH=C=CH$_2$.

"Acyloxy" refers to the group —OCOR wherein R is allkyl as herein defined; "Carboxylate" refers to the group —COOH, and "carboalkoxylate" refers to the group —COOR wherein R is alkyl as herein defined.

"Halo" refers to any of the common halo substituents including fluoro-, chloro-, bromo-, and iodo-.

The "oxo form" refers to those compounds of Formula 1 which are oxidized forms of the 1-hydroxyalkyl embodiments wherein the substituent at C-13 is —COR$_1$. The "carboxylic acid form" refers to those compounds of Formula 1 which are oxidized forms of the hydroxymethyl embodiments wherein the substituent at C-13 is —COOH or the alkyl esters thereof.

A Grignard moiety, "M" represents an electropositive group which can be used to transfer organic radicals as anions, in a manner similar to that of the classical Grignard moiety, MgBr.

The conventional steroid numbering system and backbone are used herein, and for convenience are set forth below:

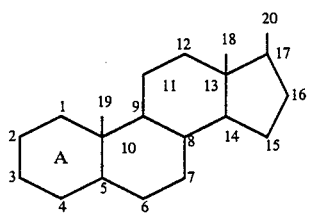

"Pharmaceutically acceptable esters" refers to acyl substituted derivatives of the free alcohol on C-17 which are derived from the carboxylic acids of the formula RCOOH wherein R is alkyl as herein defined.

Certain of the embodiments of the invention also contain hydroxyl groups on ring A or B at their fusion, such hydroxyl groups can, of course, be esterified or converted to ethers. In addition, when A is aromatic and $R^1$ is H, this represents an acidic hydrogen, and accordingly the pharmaceutically acceptable salts are also included within the scope of the invention. Such salts include those of inorganic bases such as sodium hydroxide, potassium hydroxide, ammonium hydroxide, calcium hydroxide and so forth and also those of organic bases such as trimethylamine, lysine, caffeine, and the like.

Certain of the carbons in some embodiments of compounds of the invention and of the intermediates in their preparation are chiral centers whose stereochemistry is not specified. Of course, the stereochemistry of the ring system of the steroids per se is known, and it is understood that the stereochemistry in the natural product is retained in those compounds of the invention directly prepared from the natural product. However, in other instances, such as those wherein C-17 of the opened system is chiral, both individual stereoisomers and mixtures thereof, are intended to be included unless otherwise designated. This is true also of the products of manipulation of the A and B rings, where bonds affecting the chirality are made and broken. If the chirality of these carbons is intended to be shown, the conventional designations R or S will be used; otherwise, the chirality will be considered undetermined—Fischer projections are not intended in any of the formulas drawn. If desired, mixtures of the diastereomeric forms of the compounds may be resolved into their separate optical antipodes by conventional resolution means, for example, by separation using fractional crystallization, chromatography, or other standard means known in the art for separation of compounds.

In addition, certain embodiments of the compounds of the invention and certain intermediates in their preparation contain double bonds capable of E,Z-isomerism. Here, too, mixtures usually result, although a particular stereoisomer often predominate. Unless specifically indicated as the E or Z form, the stereoisomerism surrounding this double bond will be understood to be undetermined and may consist of either form, or of mixtures, even though a particular, arbitrarily chosen isomer may be shown.

MODES OF PREPARATION

Compounds of the invention are prepared by the reaction schemes shown below and generally result in mixtures of diastereomers, which may be separated, if desired, as indicated above. Isolation and purification of compounds and intermediates in the reaction schemes described can be effected by suitable separation or purification procedures such as filtration, extraction, crystallization, column chromatography, thin layer chromatography or a combination of these procedures.

Preparation of Pivotal Precursor Compounds

In general, the precursors to many of the compounds of the invention, from which the invention compounds are directly prepared, are obtained using the series of reactions shown in Reaction Scheme 1. Both the aldehyde form (8) and the ester form (6) can be sued to obtain the other compounds of the invention; in addition, these forms also have the desired property of 17-HSD inhibition.

Reaction Scheme 1

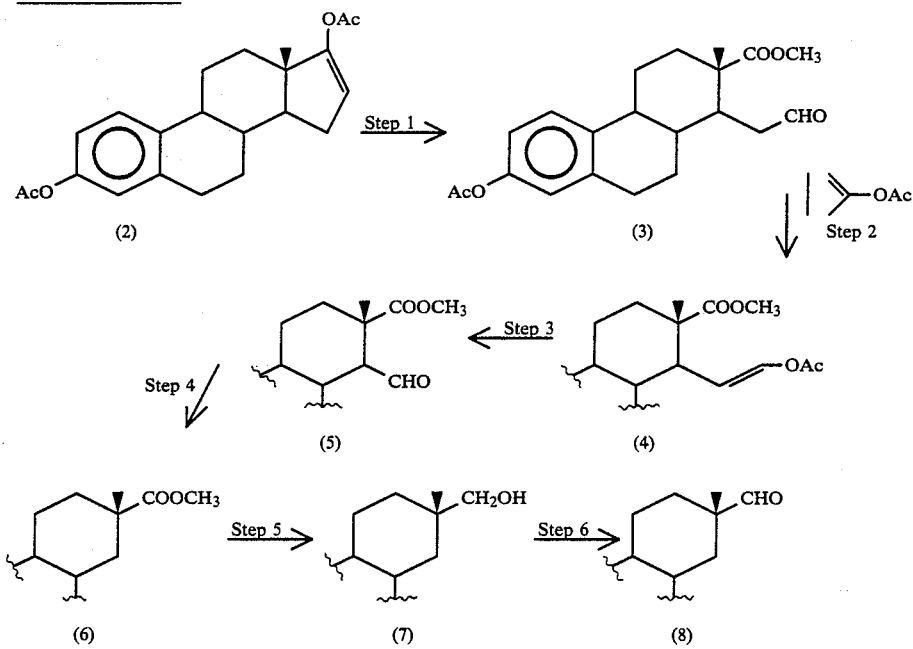

Reaction Scheme 1 involves first opening the D ring of precursor steroid by cleaving the enol acetate of the appropriate 17-keto-steroid. This is followed by degradation of the substituent at C-14. The acetylated form of the appropriate steroid, which is shown as the starting material of Reaction Scheme 1, compound (2), is prepared by conventional means known in the art, such as an exchange reaction with an appropriate enol acetate, such as isopropenyl acetate. The hydroxyl group on ring A will correspondingly be acetylated, unless it has already been derivatized in some other manner. (The A ring of Reaction Scheme 1 must either be aromatic or a completely saturated ring system, since the first step of this reaction scheme involves ozonolysis of double bonds, which would destroy isolated double bonds in the A ring, as well as effecting the desired reaction. The aromatic form of the A ring is shown for convenience.)

The cleavage of ring D in step 1 is conveniently conducted by ozonolysis: The starting material of Formula 2 is treated with ozone in methylene chloride/acetic acid, promptly followed by contacting the reaction mixture with dimethyl sulfide and then aqueous acetic acid. The produce is then esterified with, for example, diazomethane. The conditions of ozonolysis and esterification are understood for the conduct of these reactions by the practitioners of the art.

The conversion of the aldehyde obtained from ozonolysis to the corresponding enol acetate is effected in Step 2 by treating the aldehyde with isopropenyl acetate in the presence of sulfuric acid or p-toluene sulfonic acid: The compound of Formula 3 is treated with an excess of the isopropenyl acetate reagent under reflux, and the product of the exchange reaction is purified by column chromatography. A mixture of the E and Z forms of the enol acetate is obtained.

The resulting enol acetate is then subjected to ozonolysis in a manner analogous to that of Step 1 to obtain the carboxyaldehyde of Formula 5. The reaction conditions are similar to those of Step 1.

Removal of this carboxyaldehyde substituent generated in Step 3 is effected in Step 4 by treating with a decarbonylating reagent, such as tris-)triphenyl phosphene)rhodium(I) chloride. In this reaction, the decarbonylating reagent is supplied in a metal coordinating solvent such as benzonitrile in the presence of an inert atmosphere such as nitrogen or argon at about 100°–150° C., using a slight excess of the reagent. The reaction is worked up and the product isolated by conventional means to obtain the carbomethoxyl derivative of the partially hydrogenated phenanthrene analog shown as Formula 6.

Step 5 effects the reduction of the carbomethoxy compound to the corresponding alcohol, which is then oxidized to the aldehyde in Step 6. The reduction can be carried out by any convenient reducing agent, such as lithium aluminum hydride, or preferably diisobutyl aluminum hydride. Any acylation of ring A is concomitantly removed in this step.

The resulting α-hydroxymethyl compound (7) is then converted to the aldehyde in the presence of a mild oxidizing agent such as generated from a mixture of oxalyl chloride and dimethylsulfoxide. The resulting compound (8) then forms the starting material for any of the variety of compounds which constitute the steroid metabolic regulators of the invention. Compound (6) is useful for the preparation of compounds wherein $R_1$ and $R_2$ are identical and derived from an organometallic reagent.

Conversion to Additional Compounds of the Invention

The conversion of the compound of Formula 8 to other compounds of the invention is shown in Reaction Scheme 2a.

Reaction Scheme 2a

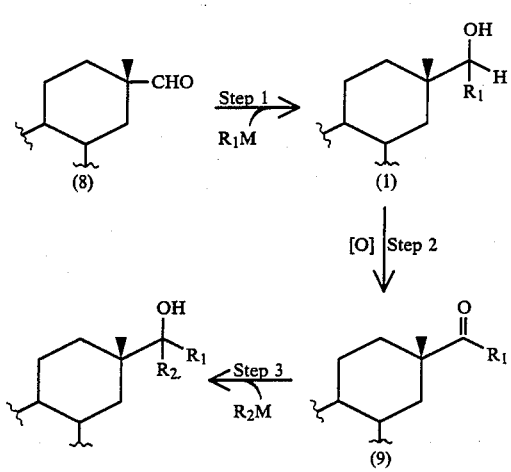

Reaction Scheme 2b

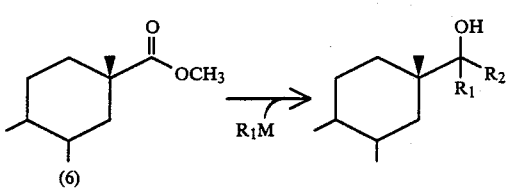

including H, halo, $CF_3$, alkoxy, alkylthio, and alkyl(-1-6). The resulting compounds of Formula 1, as shown in Reaction Scheme 2, can then optionally be converted to the corresponding allyl compounds by hydrogenation of the acetylenic bond, or converted to the allene forms by treating the product wherein $R_3$ is H with cuprous bromide and formaldehyde in the presence of diisopropylamine, or other suitable polar solvent.

Further conversion of the compounds of Formula 1 wherein $R_2$ is H to those wherein $R_2$ is not hydrogen is conducted, as there shown, by oxidation of the alcohol using, for example, Jones reagent or reagents which do not oxidize double bonds (if $R_1$ does contain double or triple bonds), or with any conventional oxidizing agent where $R_1$ is alkyl, to obtain the immediate ketone of Formula 9, which is then converted to the compounds of Formula 1 wherein $R_2$ is a nonhydrogen substituent by a Grignard-type reaction similar to that of Step 1. Of course, the order of steps 1 and 3 can be interchanged.

Compounds of Formula 1 wherein $R_1 = R_2$ may also be prepared by a Grignard type reaction similar to that of Step 1 of Scheme 2a using a compound of formula (6) as substrate (Scheme 2b).

Modification of the A Ring

Reaction Scheme 3 shows the general procedure for obtaining the various modifications of the A ring starting with an aromatized A ring and wherein the B ring remains unchanged from the starting material, i.e., remains saturated starting from:

Reaction Scheme 3

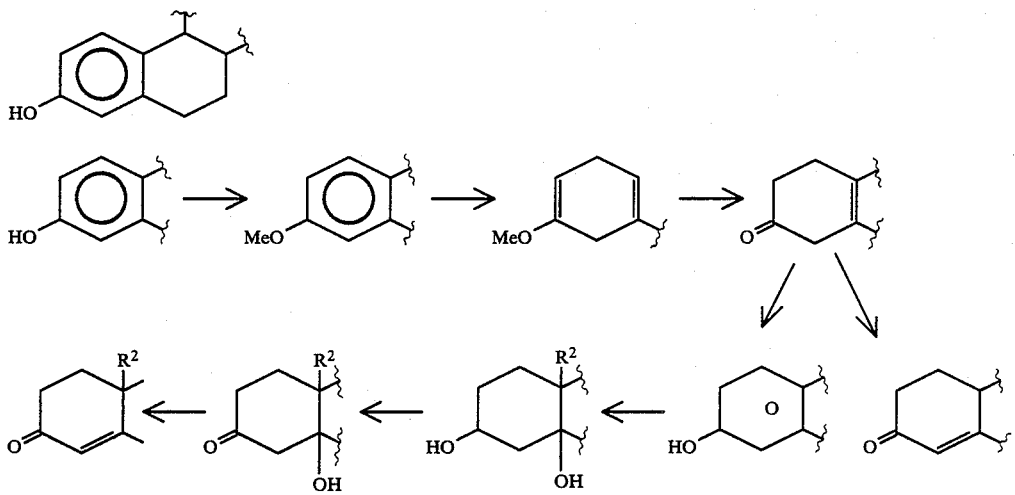

As shown, for those embodiments wherein $R_2$ is H, Step 1 suffices to prepare the compounds of the invention, or immediate precursors thereto which involve conversions in the $R_1$ substituent per se. For the embodiments in the oxidized (oxo) form, Step 2 is also required.

Step 1 is most conveniently conducted as a conventional Grignard reaction supplying $R_1$ as a traditional magnesium halide Grignard reagent or as an organolithium compound. Thus, for Step 1, $R_1$ can be any substituent which does not have substituents which interfere, and includes, for example, alkyl(1-6) or acetylenic compounds of the formula $C \equiv CR_3$, wherein $R_3$ is any group not interfering with a Grignard-type reaction, As shown in Reaction Scheme 3, starting with the aromatic form of the A-ring, and protecting the hydroxyl with an alkyl group (exemplified by methyl here), the A ring can be reduced sequentially to contain one or two (or no) isolated double bonds. Further, the double bond at the fusion of the A and B ring may be subjected to treatment by alkaline hydrogen peroxide to obtain the corresponding epoxide, which can then be reduced in the presence of a suitable Grignard reagent of the formula $R^2MgBr$ to obtain the corresponding alcohol.

If the A ring is originally saturated, it can be oxidized as shown in Scheme 4 to obtain the corresponding ketone having zero, one, or two isolated double bonds.

Step 1 of Reaction Scheme 4 is an oxidation with, for example, Jones reagent to a ketone as shown, and the resulting ketone is subsequently dibrominated in Step 2 with bromine in acetic acid/hydrobromic acid. This dibromide is either converted to the dienone as shown in Step 3 with, for example, anhydrous lithium carbonate and anhydrous lithium bromide in dimethylformamide at 100° C. or in two steps to the simple enone by first converting it to the monobromoenone, as shown in Step 4a using the same reagents as those for Step 3, but at 60° C.; the resulting monobromoenone can then be dehalogenated with zinc in acetic acid to give the enone as shown in Step 4b.

The enone can then be converted in a two step reaction shown as Steps 5a and 5b to the corresponding compound having a hydroxyl at position 4 of the steroid system. The enone is first converted to the epoxide by treating with alkaline hydrogen peroxide (in a manner analogous to that of Reaction Scheme 3), and then the α-hydroxyenone is formed via acid-catalyzed opening of bromodienone in collidine (Kaufmann, St., et al, *J Am Chem Soc* (1950) 72:4531–4534).

Utility and Administration

The compounds of the invention are useful for controlling conditions which are affected by steroid hormone metabolism. They are formulated according to conventional methods, and may be administered systemically by injection subcutaneously, intravenously, or intraperitoneally, as well as by oral or transdermal administration. The pharmaceutical compositions containing these compounds will, of course, depend on the route of administration.

Parenteral administration is generally characterized by injection, whether subcutaneously, intramuscularly, or intravenously. Injectables can be prepared in conventional forms, either as solutions or suspensions, in solid forms suitable for solution or suspension in liquid prior to injections, or as emulsions. Suitable excipients include water, saline, dextrose, glycerol, and the like. If desired, the

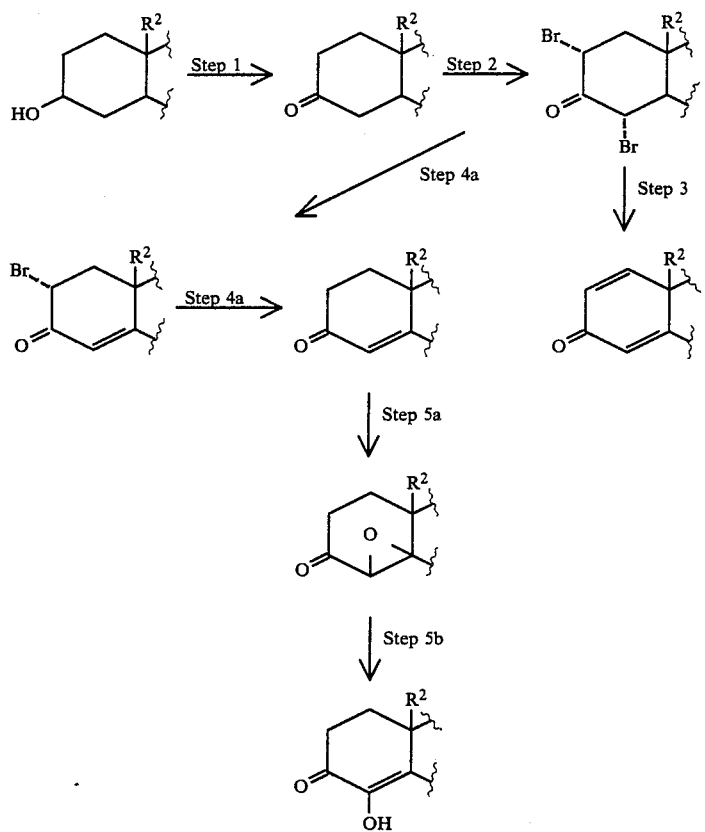

Reaction Scheme 4 the intermediate α-epoxyketone (Brodie, A. M. H., et al, *Endocrinology* (1977) 100:1684–1695).

Modification of the B Ring

Either the enone or the dienone can then be used as shown in Reaction Schemes 5 and 6 to obtain modifications of the B ring. In Reaction Scheme 5 the enone is converted in two steps with the α-hydroxyenone with subsequent Jones oxidation of this intermediate (Gardi, R., et al, *J Org Chem* (1967) 32:2647–2649).

In Reaction Scheme 6, the dienone is converted to the trienone by dehydrobromination of the intermediate Reaction Scheme 5

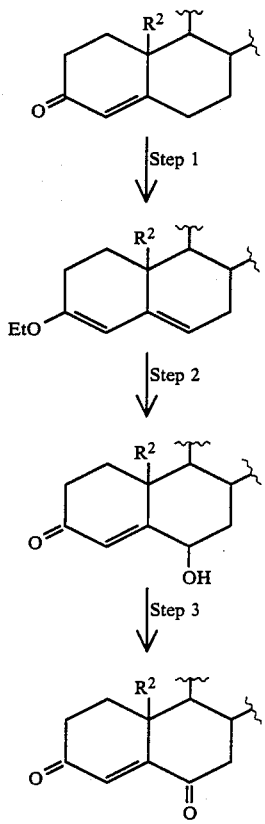

Reaction Scheme 6

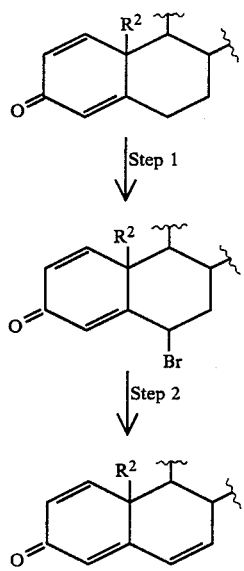

pharmaceutical compositions may also include minor amounts of nontoxic auxiliary substances, such as wetting or emulsifying agents, pH-buffering agents, and so forth.

For oral administration, the active ingredient is generally administered as a syrup, capsule, or tablet, and pharmaceutically nontoxic compositions are formed using the normally employed excipients, such as pharmaceutical grades of mannitol, lactose, starch, magnesium stearate, talcum, cellulose, magnesium carbonate, and so forth. The compositions include sustained release formulations and contain 10-95% active ingredient, with the remainder carrier, as a general rule.

For administration via suppository, traditional binders and carriers include, for example, polyalkylene glycols or triglycerides, and the suppositories generally contain active ingredient in the range 0.5-10%. Standard methods of formulating compounds for administration as pharmaceuticals can be found in Remington's Pharmaceutical Sciences, Mack Publishing Company, Easton, Pa., latest edition.

The amount of active compound to be administered depends on the subject being treated, the severity of the condition being treated, the manner of administration, and the judgment of the physician. However, an effective dose is in the range of 5-500 mg/day per typical subject.

Preferred Embodiments

Preferred among the compounds of the invention are those wherein ring A is aromatic and wherein $R^1$ is H or acyl. Also preferred are those wherein rings A and B are as shown in Table 1, and those in which rings A and B are selected from:

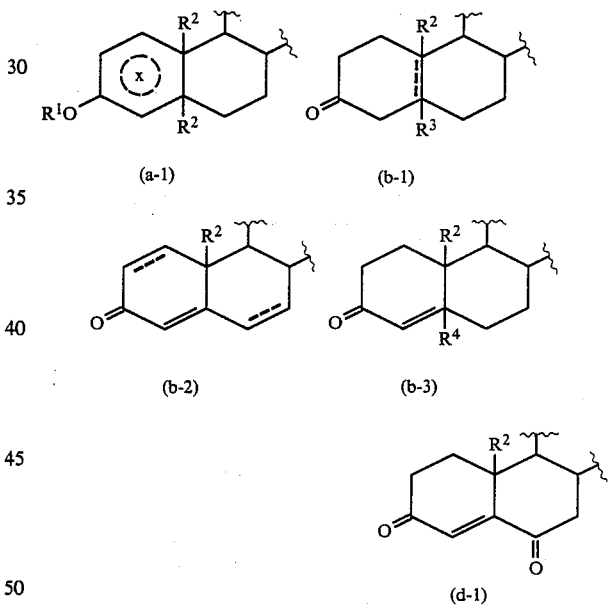

Wherein $(x)$, the dotted line, and the various superscripted Rs are as herein defined.

Among preferred embodiments are those compounds wherein at least one of $R_1$ and $R_2$ is selected from:

$$-C\equiv CR_3, -CH=CHR_3, \text{ or } -CH=C=CHR_3,$$

particularly wherein $R_3$ is H, alkyl(1-6), or alkoxy, and, more particularly, wherein $R_1$ is:

$$-C\equiv CH, CH=C=CH_2, \text{ or } -C\equiv COEt.$$

Also among preferred embodiments are those wherein at least one of $R_1$ and $R_2$ is H or alkyl (especially methyl) and wherein $R_1$ and $R_2$ are identical.

Also preferred are the oxo and carboxylic forms of the compounds of Formula 1.

The following table sets forth representative examples of the preferred compounds of the invention.

TABLE 1

| A | Substituent at C-13 |
|---|---|
| (structure: 6-hydroxy-tetrahydronaphthalene with HO-) | —CH(OH)C≡C—OCH$_2$CH$_3$ |
| " | —COC≡C—OCH$_2$CH$_3$ |
| " | —CH$_2$OH |
| " | —CHO |
| " | —COOR (R = H, alkyl) |
| " | —COCH$_3$ |
| " | —CH(OH)CH$_3$ |
| " | —CH(OH)C≡CH |
| " | —COC≡CH |
| " | —C(OH)CH$_3$ <br> \| <br> CH$_3$ |
| " | —C(OH)C≡CH <br> \| <br> C≡CH |
| " | —C(OH)C≡CH <br> \| <br> CH$_3$ |
| (structure: dienone with R$^1$) | —CH(OH)C≡C—OCH$_2$CH$_3$ |
| " | —COC≡C—OCH$_2$CH$_3$ |
| " | —CH$_2$OH |
| " | —CHO |
| " | COOR (R = H, alkyl) |
| " | —COCH$_3$ |
| " | —CH(OH)CH$_3$ |
| " | —CH(OH)C≡CH |
| " | —COC≡CH |
| " | —C(OH)CH$_3$ <br> \| <br> CH$_3$ |
| " | —C(OH)C≡CH <br> \| <br> C≡CH |
| " | —C(OH)C≡CH <br> \| <br> CH$_3$ |
| (structure: cyclohexenone with OH and R$^2$) | —CH(OH)C≡C—OCH$_2$CH$_3$ |
| " | —COC≡C—OCH$_2$CH$_3$ |
| " | —CH$_2$OH |
| " | —CHO |
| " | —COOR (R = H, alkyl) |
| " | —COCH$_3$ |
| " | —CH(OH)CH$_3$ |
| " | —CH(OH)C≡CH |
| " | —COC≡CH |
| " | —C(OH)CH$_3$ <br> \| <br> CH$_3$ |
| " | —C(OH)C≡CH <br> \| <br> C≡CH |
| " | —C(OH)C≡CH <br> \| <br> CH$_3$ |
| " | —CH(OH)C≡C—OCH$_2$CH$_3$ |
| (structure: octahydro bicyclic enone with R$^2$ and ketone) | |
| " | —COC≡C—OCH$_2$CH$_3$ |
| " | —CH$_2$OH |
| " | —CHO |
| " | —COOR (R = H, alkyl) |
| " | —COCH$_3$ |
| " | —CH(OH)CH$_3$ |
| " | —CH(OH)C≡CH |
| " | —COC≡CH |
| " | —C(OH)CH$_3$ <br> \| <br> CH$_3$ |
| " | —C(OH)C≡CH <br> \| <br> C≡CH |
| " | —C(OH)C≡CH <br> \| <br> CH$_3$ |

EXAMPLES

The following examples are intended to illustrate but not limit the invention. Whereas the usually used steroid numbering system was used in the discussion of the invention in general, the examples below employ the numbering system associated with the open-chain phenanthrene analog.

EXAMPLE 1

Preparation of Methyl [1S-(1α,2β,4aβ,10aβ)]-7-(acetyloxy)-1,2,3,4,4a,9,10,-10a-octahydro-2-methyl-1-(2-oxoethyl)-2-phenanthrenecarboxylate A solution of estra-1,3,4(10),16-tetraene-3,17-diol diacetate (1.42 g, 4 mmol) in methylene chloride (40 mL) and glacial acetic acid (3.2 mL) was chilled to −78°. Ozone from a Weilsbach generator was bubbled into the solution through a gas dispersion tube at a rate of 1.2 L/min until the reaction mixture became bright blue (less than 5 min). Dimethyl sulfide (0.6 mL, 8 mmol) was added with stirring, and the reaction mixture was warmed to 0°. Glacial acetic acid (36.8 mL), then distilled water (12 mL) were added, and the reaction mixture was stirred at room temperature for 5 h when no anhydride remained (disappearance of the 1811 cm$^{-1}$ absorbance). The reaction mixture was poured into 100 mL each water and methylene chloride, shaken, and separated. The organic layer was washed with 100 mL water and 50 mL saturated sodium chloride solution, dried over sodium sulfate, filtered, and concentrated in vacuo to a clear, colorless oil. The residue was taken up in 10 mL diethyl ether, chilled to 0°, and treated with an excess of ethereal diazomethane (30 mL of an appx. 0.35M solution). The reaction mixture was coated on 3 g silica gel and purified by flash chromatography on 30 g silica gel, eluting with a stepwise gradient of ethyl acetate in hexane. The title compound eluted with 20% ethyl acetate in hexane. Concentration of the eluate in vacuo afforded 1.31 g white plates (92% yield), mp 98°-101°.

IR: 2722, 1757, 1723, 1209 cm$^{-1}$
MS: M$^+$=358 m/z
Elemental Analysis: Calc.: C, 70.37%; H, 7.31%. Obs.: C, 70.51. %; H, 7.34%.

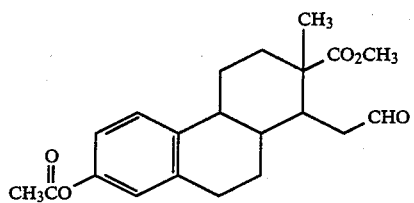

EXAMPLE 2

Preparation of Methyl [1R-(1α,2β,4aβ,10aα)]-7-(acetyloxy)-1-{2-(acetyloxy)ethenyl]-1,2,3,4,4a,9,10,10a-octahydro-2-methyl-2-phenanthrenecarboxylate A solution of the aldehyde prepared in Example 1 (1.31 g, 3.65 mmol) in isopropenyl acetate (20 mL) with p-toluenesulfonic acid (50 mg) was set to reflux beneath a short Vigreaux column equipped with a short-path condensor and a drying tube for 22 h. Periodically, about 10 mL distillate was collected by raising the reaction temperature, and fresh isopropenyl acetate plus additional p-toluenesulfonic acid were added (a total of 55 mL isopropenyl acetate and 100 mg p-toluenesulfonic acid were employed). The reaction mixture was cooled to room temperature, poured into 50 mL each diethyl ether and dilute aqueous sodium bicarbonate, shaken, and separated. The organic layer was washed with 50 mL water and 25 mL saturated sodium chloride solution, dried over sodium sulfate, filtered and concentrated in vacuo to a red oil. The crude product was coated on 3.5 g silica gel and purified by flash chromatography on 25 g silica gel with a stepwise gradient of ethyl acetate in hexane (the enol acetates eluted with 15% ethyl acetate in hexane). The solvent was removed in vacuo to give 1.23 g of a white foam (84% yield).

IR: 1757, 1734, 1669, 1211 cm$^{-1}$
MS: M$^+$=400 m/z.
Elemental Analysis: Calcd.: C, 68.98%; H, 7.05%. Obsd.: C, 69.21, H, 7.06%.

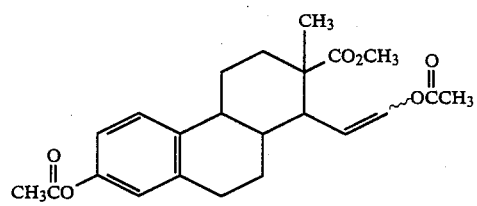

EXAMPLE 3

Preparation of Methyl [1S-(1α,2β,4aβ,10aα)]-7-(acetyloxy)-1-formyl-1,2,3,4,4a,9,10,10a-octahydro-2-methyl-2-phenanthrenecarboxylate A solution of the enol acetates of Example 2 (1.23 g, 3.0 mmol) was dissolved in methylene chloride (30 mL) and glacial acetic acid (2.4 mL) and chilled to −75°. Ozone was bubbled into the reaction mixture through a gas dispersion tube (1.2 L/min) until a faint blue color persisted (appx. 5 min). Dimethyl sulfide (0.45 mL, 6 mmol) was added with stirring, and the reaction mixture was warmed to room temperature over 15 min. Distilled water (190 μL) was added, and the reaction mixture was stirred at room temperature for 1 h. The reaction mixture was washed twice with 20 mL water and once with 15 mL saturated sodium chloride solution, dried over sodium sulfate, filtered, and concentrated in vacuo to a pale yellow oil. Application of a high vacuum (<1 mm Hg) prompted the formation of white crystals. The crystals were heated in a small amount of diethyl ether and then chilled on ice. The solvent was aspirated, and the crystals were washed with cold hexane, affording 895 mg small white leaflets (87% yield), mp 111°-115°. Recrystallization from methylene chloride/hexane afforded white prisms, mp 121°-124°.

IR: 2736, 1757, 1723, 1211 cm$^{-1}$.
MS: M$^+$=344 m/z
Elemental Analysis: Calc. C, 69.75%; H, 7.02%. Obs.: C, 69.67%; H, 7.13%.

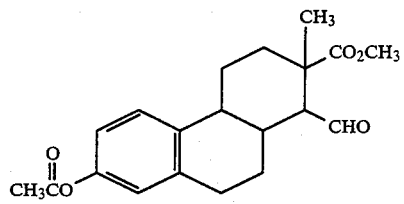

EXAMPLE 4

Preparation of Methyl [2S-(2α,4aα,10aβ)]-7-(acetyloxy)-1,2,3,4,4a,9,10,10a-octahydro-2-methyl-2-phenanthrenecarboxylate Aldehyde of Example 3 (1.74 g, 5 mmol) and tris (triphenylphosphine) rhodium [I] chloride (4.77 g, 5 mmol) was heated under nitrogen at 135° in benzonitrile (25 mL) for 5.5 h as the deep burgundy red solution gradually grew lighter in color. Upon cooling, a yellow solid deposited from the solution. Most of the benzonitrile was removed by careful distillation at reduced pressure, and the warm suspension was stirred while adding 50 mL absolute ethanol. After chilling, the greenish-yellow solid was filtered off and washed with absolute ethanol, giving 3.53 g of rhodium complex. The filtrates were concentrated in vacuo to a red oil which was coated on 7 g silica gel and purified by flash chromatography on a column of 60 g silica gel with a stepwise gradient of ethyl acetate in hexane. Leftover benzonitrile was thoroughly eluted with 5% ethyl acetate in hexane before eluting the product with 7.5%-10% ethyl acetate in hexane. Removal of solvents in vacuo afforded 1.40 g (89% yield) of a clear, slightly brownish oil. The oil solidifies on standing at −20° and may be recrystallized from hexane to give white prisms, mp 58°-61°. It is advisable to chill the crude reaction mixture and to filter off the yellow complex before distillation to maximize removal of benzonitrile. It is also essential to exclude oxygen from the reaction.

IR: 1757, 1726, 1213 cm$^{-1}$.
MS: M$^+$=316 m/z
Elemental Analysis: Calc.: C, 72.13%; H, 7.65%. Obs.: C, 72.15%; H, 7.73%.

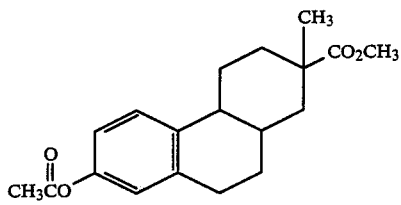

EXAMPLE 5

Prparation of [2S-(2α,4aα,10aβ)]-1,2,3,4,4a,9,10,10a-Octahydro-7-hydroxy-2-methyl-2-phenanthrenemethanol A solution of the ester of Example 4 (1.71 g, 5.5 mmol) in toluene (50 mL) was chilled to −78° under nitrogen and treated with an excess of diisobutyl aluminium hydride (62 mL of a 1.0M solution in toluene) in a dropwise stream. After 15 min, the stirred reaction mixture was cautiously treated with 100 mL saturated ammonium chloride solution and 150 mL 10% hydrochloric acid to decompose the aluminum alkyl) producing vigorous gas evolution) and to dissolve the gelatinous aluminum hydroxide. The aqueous layer was back-extracted twice with 50 mL ethyl acetate, and the pooled organic layers were washed with 75 mL water and filtered. Removal of solvent in vacuo precipitated a white solid that was recrystallized from diethyl ether/hexane (plus a small amount of ethyl acetate to complete dissolution) and afforded two crops of white prisms, 1.15 and 0.05 g, mp 139°-142° (total, 1.2 g, 90% yield).

IR: 3330 cm$^{-1}$.
MS: M$^+$=246 m/z
Elemental Analysis: Calc.: C, 78.01%; H, 9.00%. Obs.: C, 77.79%; H, 8.88%.

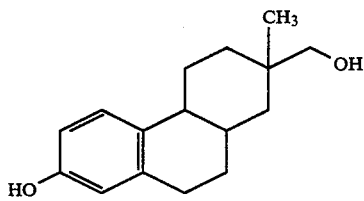

EXAMPLE 6

Preparation of [2S-(2α,4aα,10aβ)]-1,2,3,4,4a,9,10,10a-Octahydro-7-hydroxy-2-methyl-2-phenanthrenecarboxaldehyde A solution of oxalyl chloride (0.64 mL, 7.3 mmol) in methylene chloride (15 mL) was chilled to −60° under nitrogen. Dimethyl sulfoxide (1.05 mL, 14.7 mmol) in methylene chloride (3 mL) was added dropwise to the stirred solution, producing vigorous gas evolution during the first half of the addition. After stirring at −60° for 5 min, a solution of the alcohol of Example 5 (1.2 g, 4.9 mmol), dissolved in 1.5 mL dimethyl sulfoxide and diluted with 3.5 mL methylene chloride, was added in a steady stream. A white precipitate formed as the reaction mixture was warmed to −10° over 30 min. The reaction mixture was then chilled to −50° and treated dropwise with triethylamine (3.4 mL, 24.5 mmol). The suspension was poured into 120 mL ethyl acetate which was washed twice with water and once with saturated sodium chloride solution (50 mL each time), dried over sodium sulfate, and filtered. The crude product was coated on 4 g silica gel and purified by flash chromatography on 25 g silica gel with a stepwise gradient of ethyl acetate in hexane (the product eluted with 20% ethyl acetate in hexane). Removal of solvents in vacuo and recrystallization from diethyl ether/hexane or methylene chloride/hexane (plus enough ethyl acetate to complete dissolution) gave two crops of white prisms, 712 mg combined. Further chromatography of the mother liquors produced another 104 mg for a total of 816 mg (69% yield), mp 159°-163°.

IR: 3405, 2711, 1721 cm$^{-1}$.
MS: M$^+$=244 m/z.
Elemental Analysis: Calc.: C, 78.655; H, 8,25%. Obs.: C, 78.40%; H, 8.23%.

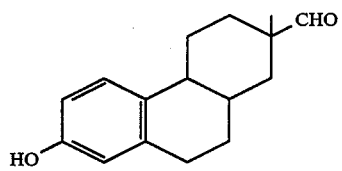

EXAMPLE 7

Preparation of [2S-[2α(S*),4aα,10aβ]]-α-Ethynyl-1,2,3,4,4a,9,10,10a-octahydro-7-hydroxy-2-methyl-2-phenanthrenemethanol Acetylene (passed through a −70° trap and H$_2$SO$_4$) was bubbled into tetrahydrofuran (freshly distilled from lithium aluminum hydride, 30 mL) for 5 min. before and during the dropwise addition of methyl magnesium bromide in diethyl ether (2 mL, 4 mmol). Acetylene was bubbled into the clear, purple solution for another 30 min. when the evolution of small gas bubbles ceased. Nitrogen was passed over the ethynyl magnesium bromide solution and the aldehyde of Example 6 (195 mg, 0.8 mmol) in dry tetrahydrofuran (2 mL) was added dropwise, followed by two rinses with tetrahydrofuran (1 mL each). Vigorous stirring was necessary to disperse the gelatinous white precipitate that formed during the addition of the aldehyde. After stirring at room temperature for 15 min., the reaction mixture was poured into 80 mL each ethyl acetate and saturated ammonium chloride solution, acidified with 5 mL 10% HCl, shaken, and separated. The organic layer was washed with 70 mL saturated sodium chloride solution, dried over sodium sulfate, filtered, and concentrated in vacuo. The residue was coated on 1 g silica gel and purified by flash chromatography on 10 g silica gel with a stepwise gradient of ethyl acetate in hexane (the product eluted with 20-25% ethyl acetate in hexane). The concentrated eluates were crystallized with diethyl ether and hexane, affording 87 mg (40% yield) amorphous white solid plus prisms, mp 191°-197°. A second crop of crystals )4.5 mg, mp 195°-197°) was obtained, and the mother liquors (appx. 100 mg white foam) were suitable for further use without additional purification. The total yield was 80–85%.

IR: 3400, 3261, 2115 cm$^{-1}$.
MS: M+ =270 m/z
Elemental Analysis: CAlc.: C, 79.96; H, 8,20. Obs.: C, 79.89; H, 8.18.

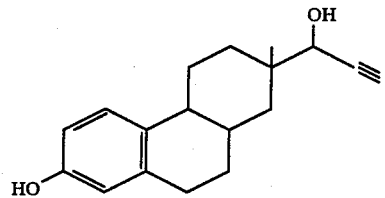

EXAMPLE 8

Preparation of [2S-(2α,4aα,10aβ)]-1-(1,2,3,4,4a,9,10,10a-Octahydro-7-hydroxy-2-methyl-2-phenanthrenyl)-2-propyn-1-one A solution of the diol of Example 8 (92 mg, 0.34 mmol) in acetone (25 mL) was chilled to 0° and treated dropwise while stirring with Jones reagent (325 μL), producing a thick, brownish green precipitate. After stirring at 0° for 5 min., two drops of methanol were added, and the reaction mixture was concentrated in vacuo at room temperature. The residue was taken up in 20 mL each ethyl acetate and water, shaken, and separated. The organic layer was washed with water (20 mL) and saturated sodium chloride solution (10 mL), dried over sodium sulfate, filtered, and concentrated in vacuo. The residue (94 mg) was applied to a pipette column of silica gel in a minimal amount of chloroform and methylene chloride and eluted with a stepwise gradient of ethyl acetate in hexane under gentle pressure (the produce eluted with 15% ethyl acetate in hexane). Recrystallization from diethyl ether and hexane gave 29 mg (32% yield) amorphous solid and plates, mp 169°–173°. Better yields are obtained if great care is taken not to exceed 1 equivalent of reagent (best yield yet obtained was 53%).

IR: 3434, 3216, 2088, 1657 cm$^{-1}$
MS: M+ =268 m/z
Elemental Analysis: Calc,: C, 80.56; H, 7.51. Obs.: C, 80.69; H, 7.62.

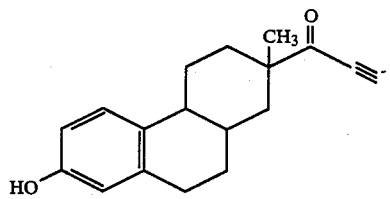

EXAMPLE 9

Preparation of [2S-(2α,4aα,10aβ)]-1,2,3,4,4a,9,10,10a-Octahydro-7-hydroxy-α,α,2-trimethyl-2-phenanthrenemethanol A stirred solution of the ester of Example 4 (2.0 g, 7.3 mmol) in freshly distilled tetrahydrofuran (300 mL) was refluxed for 45 min with methyl magnesium bromide (58 mmol in 20 mL of ether). Aqueous 5% ammonium chloride (300 mL) was then added and the organic and aqueous phases separated. The solvents were removed from the organic phase on a rotary evaporator in vacuo and the oily residue was dissolved in ethyl acetate (100 mL). The aqueous phase was extracted with diethyl ether (2×150 mL) and the ether extracts were combined with the ethyl acetate phase and dried with anhydrous magnesium sulfate. Solvent removal left an oil which was purified by column chromatography on dry column grade silica gel using 10% ethyl acetate in chloroform as eluent. The title compound was obtained as an oil (1.9 g, 95% yield) after solvent removal.

IR: 3322, 1611, 1586 cm$^{-1}$.

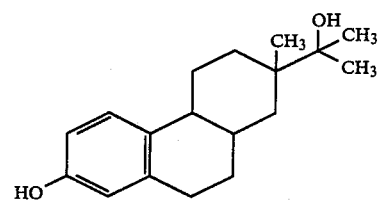

EXAMPLE 10

Preparation of [2S-(2α,4aα,10aβ)]-1,2,3,4,4a,9,10,10a-Octahydro-7-methoxy-α,α,2-trimethyl-2-phenanthrenemethanol A solution of the diol of Example 9 (1.9 g, 6.9 mmol) in methanol (200 mL) was treated with 9×50 mL portions of an ethereal solution of diazomethane (approximately 0.35M) during a 2 day period. The solvents were periodically reduced in quantity in vacuo on a rotary evaporator so that the total reaction volume did not exceed ~400 ml at any time. Following complete methylation of the phenol group the solvents were removed in vacuo and the resulting oil was column chromatographed on dry column grade silica gel using 10% ethyl acetate as eluent. The title compound was obtained as an oil )1.65 g, 82% yield) after solvent removal.

IR: 3480, 1605, 1570 cm$^{-1}$.

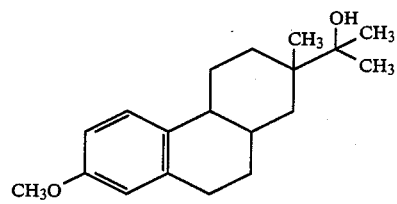

EXAMPLE 11

Preparation of [2S-(2α,4aα,10aβ)-1,2,3,4,4a,5,8,9,10,10a-Decahydro-7-methoxy-α,α,2-trimethyl-2-phenanthrenemethanol A solution of the methyl ether of Example 10 (1.65 g, 5.7 mmol) in diethyl ether (150 mL) was cooled to −35° C. in a nitrogen purged 1000 mL threeneck flask equipped with a stainless steel mechanical stirrer, a Dewar condensor filled with isopropanol and solid carbon dioxide, and a vent tube. Anhydrous ammonia from a gas cylinder was condensed in the flask until 200 mL of liquid ammonia was present and lithium metal (1.7 g) was added. After a few minutes a blue color developed and the reaction was continued an additional 10 min. Absolute ethanol (20 mL) was then added over a 15 min period, and the reaction was allowed to warm to room temperature and the ammonia was allowed to evaporate on standing overnight. Diethyl ether (250 mL) and water (250 mL) were added to the residue and both phases were transferred to a separately funnel. the aqueous phase was extracted with diethyl ether (2×100 mL) and the combined ether phases were washed with brine and dried over anhydrous sodium sulfate. Solvent removed in vacuo gave the tile compound as an oil (1.5 g, 90% yield) which was used without further purification.

IR: 3470, 1690, 1660 cm$^{-1}$.

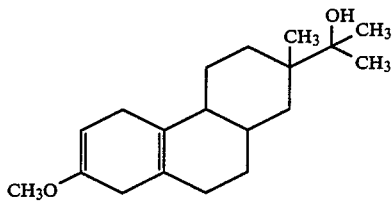

EXAMPLE 12

Preparation of [4bS-(4bα,7α,8aβ)]-3,4,4b,5,6,7,8,8a,9,10-Decahydro-7-(1-hydroxy-1-methylethyl)-7-methyl-2(1H)-phenanthrenone Enol ether of Example 11 (1.5 g, 5.2 mmol) was dissolved in a stirred solution of tert-butyl alcohol (45 mL), methylene chloride (12 mL), water (12 mL), and 70% perchloric acid (70 μL) at room temperature. After 3 hrs., 2.2% sodium bicarbonate (135 mL) and ethyl acetate (75 mL) were added, the layers were shaken and separated. The water layer was further extracted with ethyl acetate (75 mL) and the combined organic phases were washed with brine and dried over anhydrous sodium sulfate. After filtration, the solvents were removed in vacuo on a rotary evaporator to give the product as an oil (1.3 g, 91% yield) which was used without further purification.

IR: 3500, 1715, 1625 (shoulder) cm$^{-1}$.

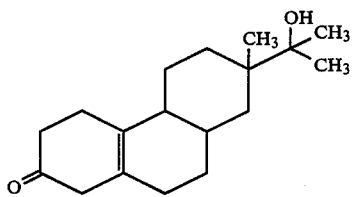

EXAMPLE 13

Preparation of [4aR-(4aα,4bβ,7β,8aα)-4,4a,4b,5,6,7,8,8a,9,10-Decahydro-7-(1-hydroxy-1-methylethyl)-7-methyl-2(3H)-phenanthrenone The unconjugated ketone of Example 12 (90 mg, 0.33 mmol) was dissolved in methanol (5 mL), 3 N hydrochloric acid (1 mL) was added, and the solution was stirred at 60° C. for 15 min. The reaction was cooled, water (20 mL) and diethyl ether (20 mL) were added, and after shaking the organic layer was separated. The aqueous layer was further extracted with diethyl ether (2×20 mL) and the combined organic layers were washed with 5% sodium bicarbonate (2×30 mL), followed by brine (2×30 mL), and then dried over anhydrous sodium sulfate. After filtration the solvents were removed in vacuo on a rotary evaporator to leave a yellow oil which was partially purified by column chromatography on a silica gel column with elution by 90% chloroform/10% tertbutyl methyl ether. Final purification was achieved by high pressure liquid chromotography on a silica gel column eluted with 80% hexane/20% acetone to give the title compound after solvent removal as a white crystalline solid (45 mg, 50% yield) which has mp 84°–86° C.

IR: 3380, 1665, 1610 cm$^{-1}$.

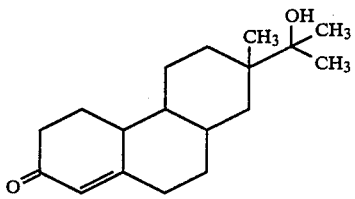

EXAMPLE 14

Preparation of [2S-(2α,4aβ,4bβ,7β,8aα,10aβ)]-Dodecahydro-2-hydroxy-α,α,7-trimethyl-4a,10a-epoxyphenanthrene-7-methanol The unconjugated ketone (1.04 g, 3,77 mmol) of Example 12 was dissolved in a stirred solution of tert-butyl alcohol (28 mL), methylene chloride (4 mL) and water (4 mL) at 0° C. and 0.6% perchloric acid (4 mL) and N-bromosuccinimide (825 mg, 4.62 mmol) were added. After 15 min the reaction mixture was cooled to −10° C. and sodium borohydride (365 mg, 9,61 mmol) was added. After stirring an additional 15 min., 1N sodium hydroxide (8.75 mL) was added and the reaction was stirred an additional 1 hr. at 0°–5° C. Ethyl acetate (100 mL) and water (100 mL) were then added and after shaking the organic and aqueous layers were separated. The water layer was further extracted with ethyl acetate (2×50 mL) and the combined organic layers were washed with water (2×50 mL), brine (2×50 mL) and dried over anhydrous sodium sulfate. Solvent removal in vacuo on a rotary evaporator gave the title compound as an oil (620 mg, 56% yield) which was used without further purification.

IR: 3350 cm$^{-1}$.

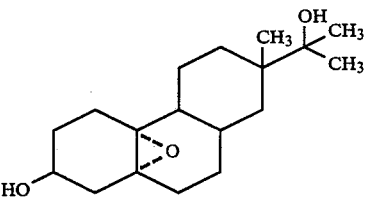

EXAMPLE 15

Preparation of [2S-(2E,4aα,4bβ,7β,8aα,10aβ)]-Tetradecahydro-2,10a-dihydroxy-α,α,7-trimethyl-4a-(2-propynyl)-7-phenanthrenemethanol The epoxide (90 mg, 0.31 mmol) of Example 14 was dissolved in stirred diethyl ether (20 mL) and propargyl magnesium bromide [10 mL of a solution freshly prepared by reacting magnesium metal (1.23 g) and propargyl bromide (5.34 g) in diethyl ether (50 mL)]was added. After 15 hrs. at room temperature, 5% ammonium chloride (50 mL) was added and the resulting two phases were separated. The aqueous phase was further extracted with diethyl ether (2×50 mL) and the combined diethyl ether fractions were washed with water (2×50 mL) and dried over anhydrous magnesium sulfate. After filtration, the ether was partially removed in vacuo and hexane was added and the solution was cooled in an ice bath. The title compound was obtained as a crystalline solid (30 mg, 29% yield) which has mp 157°–159° C.

IR: 3415, 3325, 2105 cm$^{-1}$.

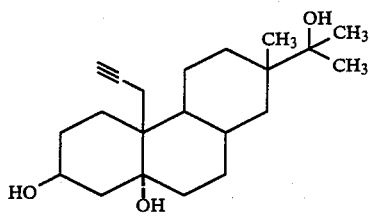

EXAMPLE 16

Preparation of [4aS-(4aα,4bβ,7β,8aα,10aβ)]-Dodecahydro-10a-hydroxy-7-(1-hydroxy-1-methylethyl)-7-methyl-4a-(2-propynyl)-2(1H)-phenanthrenone The acetylenic compound (25 mg, 0.07 mmol) of Example 14 was stirred in acetone (15 mL) with Jones reagent (0.1 mL) for 15 min. at room temperature. Methanol (0.05 mL) was then added to destroy excess oxidizing reagent, water (15 mL) was added and most of the acetone was removed in vacuo on a rotary evaporator. Methylene chloride (25 mL) was added and after shaking the two phases were separated. The aqueous phase was further extracted with methylene chloride (2×25 mL) and the combined methylene chloride layers were washed with water (2×25 mL), brine (2×25 mL), and dried over anhydrous sodium sulfate. After filtration, the solvent was removed in vacuo on a rotary evaporator to give the title compound as an oil (20 mg, 80% yield) which was used without further purification.

IR: 3450, 3320, 2105, 1710 cm$^{-1}$.

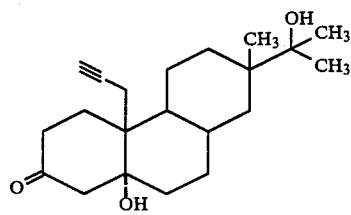

EXAMPLE 17

Preparation of [4aS-(4aα,4bβ,7b,8aα)]-4,4a,4b,5,6,7,8,8a,9,10-Decahydro-7-(1-hydroxy-1-methylethyl)-7-methyl-4a-(2-propynyl)-2(3H)-phenanthrenone The acetylenic compound (20 mg, 0.06 mmol) of Example 16 was stirred with 0.1N methanolic sodium hydroxide (3 mL) at room temperature for 1 hr. Water (5 mL) was then added and the methanol removed in vacuo on a rotary evaporator. The remaining aqueous solution was extracted with chloroform (2×20 mL) and the combined chloroform extracts were washed with water (2×20 mL) and dried over anhydrous magnesium sulfate. Solvent removal left an oil which was purified by high pressure liquid chromatography on silica gel eluted with 80% hexane/20% acetone. The title was recovered as a colorless oil (12 mg, 63% yield) which solidified on standing and had mp. 136°–138° C.

IR: 3470, 3308, 2116, 1665, 1621 cm$^{-1}$.
MS: M+314.

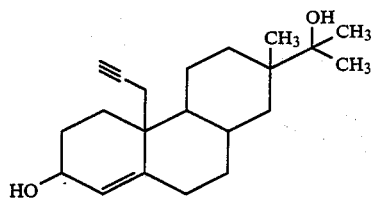

EXAMPLE 18

Preparation of Methyl [1S-(1α,2β,4aβ,4bα,7α,8aβ,10aα)]-7-(acetyloxy)-tetradecahydro-2,4b-dimethyl-1-(2-oxoethyl)-2-phenanthrenecarboxylate A solution of androst-16-ene-3β,17-diol diacetate (11.2 g, 29.9 mmol) in methylene chloride (325 mL) and glacial acetic acid (29 mL) was cooled to −78° C. Ozone was bubbled through the solution until the reaction mixture became bright blue. Dimethyl sulfide (4.5 mL) was added
and the reaction mixture was allowed to warm to room temperature. Glacial acetic acid (295) mL) and water (60 mL) were added and the reaction was stirred overnight to assure hydrolysis of the anhydride. The reaction mixture was then washed with water (3×500 mL) and brine (2×100 mL). The methylene chloride phase was then treated with an excess of ethereal diazomethane (105 mL of a 0.35M solution) and the excess diazomethane decomposed with formic acid (5 drops). The reaction mixture was the dried over anhydrous magnesium sulfate and the solvents removed in vacuo on a rotary evaporator to give an oil which was purified by column chromatography on dry column grade silica gel eluted with 15% ethyl acetate in hexane. The title compound was recovered as a colorless oil (9.0 g, 80% yield).

IR: 2720, 1729, 1244 cm$^{-1}$.

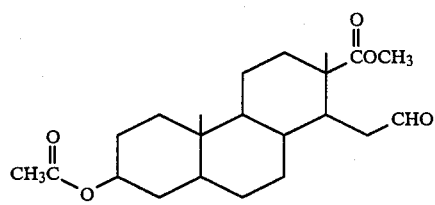

EXAMPLE 19

Preparation of Methyl [1R-(1α,2β,4aβ,4bα,7α,8aβ,10aα)]-7-(acetyloxy)-1-[2-(acetyloxy)ethenyl]-tetradecahydro-2,4b-dimethyl-2-phenanthrenecarboxylate A solution of the aldehyde of Example 18 (9.0 g, 23,8 mmol) in isopropenyl acetate (250 mL) with p-toluenesulfonic acid (2.0 g) was refluxed overnight. The reaction was cooled to room temperature and added to 20% methylene chloride in diethyl ether (250 mL). The reaction mixture was then washed with water (2×200 mL) and 5% sodium bicarbonate (2×200 mL) and then dried over magnesium sulfate. After filtration the isopropenyl acetate and organic solvents were removed in vacuo to yield a red oil which was purified by column chromatography on dry column grade silica gel eluted with 15% ethyl acetate in hexane. The title compound was recovered as an oil (12.5 g) containing trapped organic solvent. Further chromatography on silica gel partially resolved the E and Z double bond isomers of the title compound. The E-double bond isomer was a white crystalline solid with mp 171.5°–172° C.

IR: 1747, 1734, 1670, 1244, 1214 cm$^{-1}$.
Elemental Analysis: Calcd: 68.54%; H, 8,63%.
Obsd.: 68.59%; H, 8,73%.

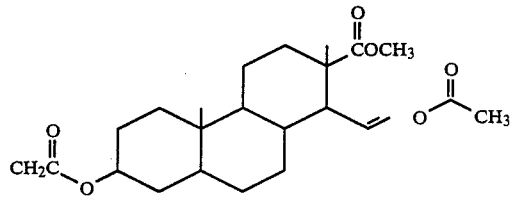

EXAMPLE 20

Preparation of Methyl [1S-(1α,2β,4aβ,4bα,7α,8aβ,10aα)]-7-(acetyloxy)-1-formyl-tetradecahydro-2,4b-dimethyl-2-phenanthrenecarboxylate A solution of the enol acetates of Example 19 (12.5 g) was dissolved in methylene chloride(275ml) and glacial acetic acid(25 ml) and cooled to −78° C. Ozone was bubbled through the solution until a blue color appeared. Dimethyl sulfide (4.5 mL) was added and the reaction was allowed to warm to room temperature. After 10 min., water (560 μL) was added and the solution was stirred an additional 45 min. The solution was then washed with water (2×200 mL), brine (1×200 mL), and dried over magnesium sulfate. Solvent removal in vacuo gave the title compound as a colorless oil (11.7 g) which solidified on standing and had mp 124°–135° C.

IR: 2729, 1732, 1243 cm$^{-1}$.

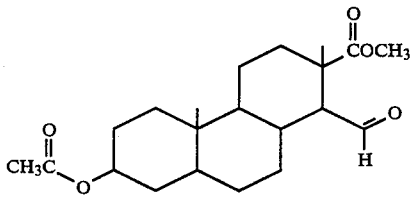

EXAMPLE 21

Preparation of Methyl [2S-(2α,4aα,4bβ,7β,8aα,10aβ)]-7-(acetyloxy)-tetradecahydro-2,4b-dimethyl-2-phenanthrenecarboxylate Aldehyde of Example 20 (13.4 g, 37.1 mmol) and tris (triphenylphosphine) rodium [I] chloride (28 g, 30.3 mmol) was heated under nitrogen at 140° C. in benzonitrile (200 mL) for ∼24 hrs. Upon cooling, a yellow solid formed and was removed by filtration. During removal of the benzonitrile in vacuo on a rotary evaporator connected to a vacuum oil pump additional yellow solid formed and was removed by filtration. After all the yellow solid and benzonitrile were removed the red oil that remained was purified by column chromatography on dry column grade silica gel. Elution was achieved with 10% ethyl acetate in hexane. The title compound was obtained as a colorless oil (9.8 g, 78%).

IR: 1733, 1243 cm$^{-1}$.

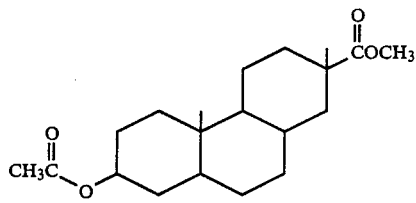

EXAMPLE 22

Preparation of Methyl [2S-(2α,4aα,4bβ,7β,8aα,10aβ)]-tetradecahydro-7-hydroxy -2,4b-dimethyl-2-phenanthrenecarboxylate The acetate of Example 21 (6.5 g, 19.3 mmol) was stirred in methanol (100 mL) to which acetyl chloride (60 drops) had been added for 4.5 hrs. at 45° C. The solvents were then removed in vacuo on a rotary evaporator to leave an oil which was purified by column chromatography on dry column grade silica gel. Elution was achieved with 30% ethyl acetate in hexane. The title compound was isolated as a colorless oil which solidified to a white crystalline solid (5.7 g, 100% yield) on standing and had mp 89°–90° C.

IR: 3382, 1729, 1240 cm$^{-1}$.
Elemental Analysis: Calc: C:73.43%, H:10.27%;Obs: C:73.50%, H:9.96%.

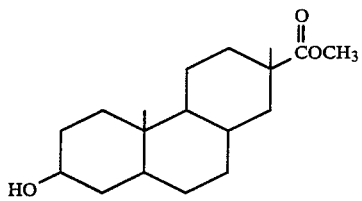

EXAMPLE 23

Preparation of Methyl [2S-(2α,4aα,4bβ,8aα,10aβ)]-tetradecahydro-2,4b-dimethyl-7-oxo-2-phenanthrenecarboxylate The alcohol of Example 22 (1.0 g, 3.4 mmol) was dissolved in acetone (130 mL) and stirred with Jones reagent (∼2.5 mL) for 20 min at room temperature. Methanol (4 mL) was added to destroy excess oxidant and then water (150 mL) was added. Removal of the acetone in vacuo on a rotary evaporator was accompanied by crystallization of the title compound from the remaining water. Filtration gave the title compound as a white crystalline solid (0.85 g, 85%) which had mp 105°–106° C.

IR: 1726, 1710, 1240 cm$^{-1}$.
Elemental Analysis: Calc:C:73.93%, H:9.65%; Obs:C:73.80%, H:9.08%.

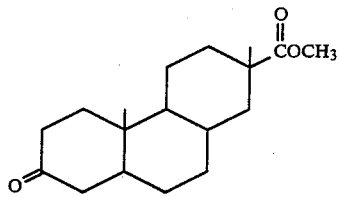

EXAMPLE 24

Preparation of Methyl
[2S-(2α,4aα,4bβ,6α,8α,8aα,10aβ)]-6,8-dibromo-tetradecahydro-2,4b-dimethy-7-oxo-2-phenanthrenecarboxylate The ketone of Example 23 (0.85 g, 2.91 mmol) was dissolved in stirred glacial acetic acid (15 mL) at 60° C. Bromine (0.93 g, 5.81 mmol) in glacial acetic acid (15 mL) was then added. The bromine solution was immediately decolorized. The reaction mixture was allowed to cool to room temperature and after 4N hydrobromic acid (1.2 mL) was added the reaction was stirred for 2.5 hrs. Water (150 mL) and methylene chloride (250 mL) were then added and after shaking, the methylene chloride layer was isolated and further washed with water (2×150 mL) and 5% sodium bicarbonate (2×150 mL). The methylene chloride was dried over anhydrous magnesium sulfate, filtered, and removed in vacuo to give the title compound as solid (1.10 g, 84% yield) which could be recrystallized from diethyl ether and had mp 172°-173° C.

IR: 1751, 1723, 1240 cm$^{-1}$.

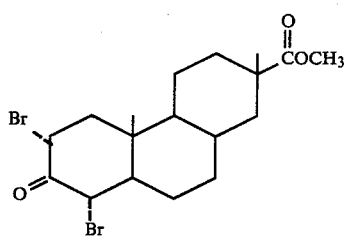

EXAMPLE 25

Preparation of Methyl
[2S-(2α,4aα,4bβ,6α,10aβ)]-6-bromo-1,2,3,4,4a,4b,5,6,7,10,10a-dodecahydro-2,4b-dimethyl-2-phenanthrenecarboxylate The dibromide of Example 24 (0.70 g, 1.56 mmol) was dissolved in dimethylforamide (20 mL) that contained anhydrous lithium bromide (840 mg, 9.65 mmol) and anhydrous lithium carbonate (840 mg, 11.35 mmol) and stirred at 60° C. for 8 hrs. The reaction mixture was filtered and the dimethyforamide removed in vacuo to yield a yellow oily solid which was dissolved in a mixture of ethyl acetate (50 mL) and water (50 mL). Following separation of the ethyl acetate layer, the water layer was extracted with ethyl acetate (50 mL), and the combined ethyl acetate fractions were washed with water (50 mL) and brine (50 mL). The ethyl acetate was dried over anhydrous magnesium sulfate, filtered, and removed in vacuo to leave a residue which was purified by column chromatography on dry column grade silica gel eluted with 25% ethyl acetate in hexane. The title compund was obtained as a white crystalline solid (432 mg, 75% yield) which had mp 139°-140° C.

IR: 1723, 1692, 1620, 1254, 1232 cm$^{-1}$.

Elemental Analysis: Calc.: C, 58.54%; H, 6.82%; Br, 21.64%. Obs.: C, 58.57%; H, 6.90%; Br, 21.79%.

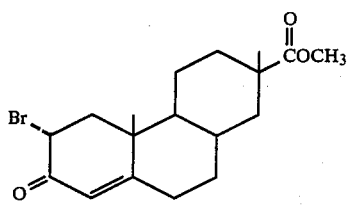

EXAMPLE 26

Preparation of Methyl
[2S-(2α,4aα,4bβ,10aβ)]-1,2,3,4,4a,4b,5,6,7,9,10,10a-dodecahydro-2,4b-dimethyl-7-oxo-2-phenanthrenecarboxylate The bromide of Example 25 (400 mg, 1.08 mml) wa dissolved in stirred glacial acetic acid (40 mL) and heated to 60° C. Zinc dust (0.75, 11.46 mmol) was added and after 20 min. the reaction was cooled. The zinc was removed by filtration the acetic acid filtrate was added to methylene chloride (125 mL). The methylene chloride was washed with water (1×100 mL, 2×75 mL) and 5% sodium bicarbonate (2×75 mL) and dried over anhydrous magnesium sulfate. Filtration and solvent removal in vacuo gave an oil which was purified by column chromatography on dry column grade silica gel. The title compound eluted with 20% ethyl acetate in hexane and was obtained as a colorless oil (228 mg, 73% yield).

IR: 1727, 1675, 1617, 1230 cm$^{-1}$.

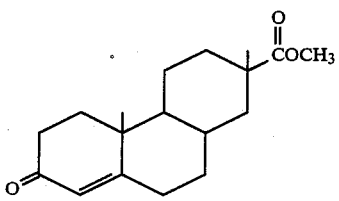

EXAMPLE 27

Preparation of Methyl
[2S-(2α,4aα,4bβ,10aβ)]-1,2,3,4,4a,4b,7,9,10,10a-decahydro-2,4b-dimethyl-7-phenanthrenecarboxylate The dibromide of Example 24 (3.0 g, 6.66 mmol), anhydrous lithium bromide (3.6 g, 43.4 mmol), and anhydrous lithium carbonate (3.6 g, 48.6 mmol) were stirred together in dimethylforamide (90 mL) at 97° C. for 6 hrs. The reaction was then filtered and the dimethylforamide was removed from the filtrate in vacuo on a rotary evaporator connected to a vacuum oil pump. The semisolid residue was dissolved in a mixture of ethyl acetate (250 mL) and water 9250 mL). The ethyl acetate layer was washed with water (2×200 mL) and dried over anhydrous magnesium sulfate. After filtration, the ethyl acetate was removed in vacuo and the residue was purified by column chromatography on dry column grade silica gel. The title compound eluted with 30% ethyl acetate in hexane and was isolated as a white crystalline solid (1.45 g, 75% yield) which had mp 105°-106° C.

IR: 1726, 1664, 1626, 1603, 1243 cm$^{-1}$.

Elemental Analysis: Calc:C: 74.97%, H:8.39%; Obs: C:75.11%, H:8.34%.

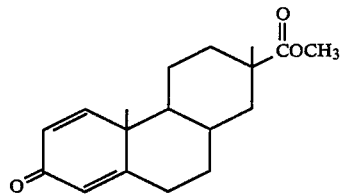

EXAMPLE 28

Preparation of
[2S-(2α,4aα,4bβ,10aβ)]-1,2,3,4,4a,4b,5,6,7,9,10,10a-Docahydro-2,4b-dimethyl-7-oxo-2-phenanthrenecarboxylic acid The enone of Example 26 (297 mg, 10.2 mmol) was dissolved in stirred methanol (15 mL) and sodium hydroxide (889 mg) dissolved in water (10 ML) was added. After 4.5 hrs., 6N hydrochloric acid (5 mL) was added. The pH of the reaction was then adjusted to ~pH5 by the addition of 5% sodium bicarbonate. Methanol was then carefully removed in vacuo until the title compound crystallized from the remaining water. The title compound (266 mg, 94% yield) had mp 217°-219° C.

IR: 2857, 1721, 1699, 1674, 1231 cm$^{-1}$.

Elemental Analysis: Calc: C:74.42%, H: 8.08%; Obs: C:74.46%, H: 8.38%.

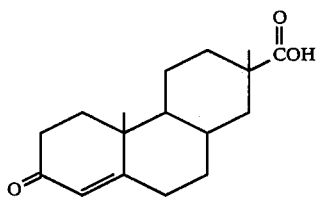

EXAMPLE 29

Preparation of
[2S-(2α,4aα,4bβ,10aβ)]-1,2,3,4,4a,4b,7,9,10,10a-Decahydro-2,4b-dimethyl-7-oxo-2-phenanthrenecarboxylic acid The dienone of Example 27 (67 mg, 0.23 mmol) was dissolved in stirred methanol (2 mL) and sodium hydroxide (192 mg) dissolved in water (2 mL) was added. After 1.5 hrs., 6 N hydrochloric acid (2.0 ml) was added and the title compound precipitated. Water (10 mL) was added and the product was isolated by filtration as white crystals (61 mg, 95% yield) which had mp 257°-259° C.

IR: 2939, 1720, 1698, 1600, 1222 cm$^{-1}$.

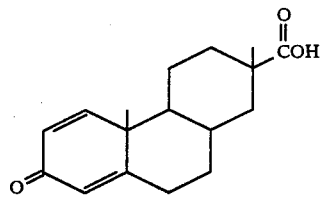

EXAMPLE 30

Characterization of Inhibitors

The compounds of the invention prepared as described above were tested for their ability to affect the reaction catalyzed by 17β-HSD, as follows.

Approximately 5 μl of a 2-20 mM solution of the test compound in absolute alcohol was added to the incubation mixture, which contained:
200 μM NAD+ (100 μl of 2 mM stock);
795 μl 100 mM sodium carbonate buffer (pH 9.2, containing 20% glycerol) or 795 μl phosphate buffer (pH 7.4, 20% glycerol);
90 μg of enzyme (supplied as 100 μl of 0.9 μg/μl stock).
Aliquots were removed at intervals and added to 950 μl of assay cocktail, which contained:
100 mM sodium carbonate buffer;
60 μM estradiol in propylene glycol stock;
200 μM NAD+; and
0.8% human serum albumin.

The activity remaining in the incubation mixture was assessed by NADH production in the assay cocktail monitored by adsorption at 340 nm every 15 sec for 2 min with an automated spectrophotometer.

All aqueous stock solutions were prepared in 100 mM sodium carbonate buffer, 20% glycerol, to maintain enzyme stability. Where additional components were added, such as glutathione, volumes were adjusted accordingly. To assess loss of enzyme activity independent of the test compound, 5 μl ethanol was added in place of steroid stock solution to the assay cocktail.

When aliquots were withdrawn less than 3 min apart, the aliquot was quenched in 900 μl assay buffer without NAD+ and supplemented with 5 mM glutathione: after all aliquots were withdrawn, samples were assayed by adding NAD+ (50 μl of a 4 mM stock) and monitored as above.

Compounds of the invention were evaluated in terms of Km, Vmax, and R$_p$. The results are as shown in Table 2.

TABLE 2

| Compound | t$_{\frac{1}{2}}$ (min) | Km (μM) | Vmax (nmol/ min/mg) | Rp (turnover/ inact.) |
|---|---|---|---|---|
| A C-13 substituent | | | | |
| —CH(OH)C≡CH | 82 | 80 | 6.5 | 7-8 |
| —COC≡CH | <10 | — | — | — |

Also given is the half life of the enzyme in the presence of optimal concentrations of the inhibitors. In each case, optimum concentration was reached at 40 μM.

For the oxidized form of the compound, inactivation of the enzyme is inhibited by the presence of NADH. Since the oxidized form is not a substrate for the enzyme in the presence of NAD+, Vmax and R$_p$ cannot be determined. In addition, 5 mM glutathione protects the enzyme from inactivation by the reduced form.

We claim:
1. A compound of the formula

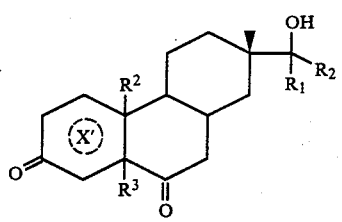

or

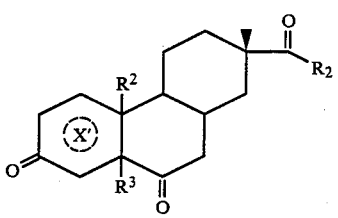

or

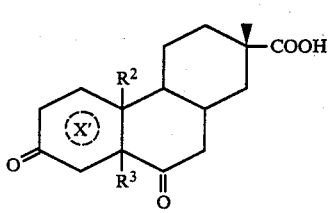

wherein (x) represents the presence or absence of 0, 1, or 2 conjugated or unconjugated π bond(s);
and wherein:
$R^2$ is H, alkyl(1-6), 2-propynyl, or allenyl;
$R^3$ is H or $OR^5$, wherein $R^5$ is H, acyl of (1-7 carbon atoms), or alkyl(1-6); and
wherein $R_1$ and $R_2$ is each independently H, alkyl(-1-6) or is —C≡$CR_3$, —CH=$CHR_3$, or —CH=C=$CHR_3$, wherein $R_3$ is selected from the group consisting of H, halo, $CF_3$, alkyl of (1-6) carbon atoms, acyloxy, carboxy carboalkoxylate, alkoxy, or alkylthio.

2. The compound of claim 1 wherein at least one of $R_1$ and $R_2$ is H.

3. The compound of claim 2 which has the formula 1B or 1C.

4. The compound of claim 1 wherein $R_1$ is H or $CH_3$, and $R_2$ is selected from the group consisting of alkyl(-1-6), —C≡$CR_3$, —CH=$CHR_3$, and —CH=C=$CHR_3$.

5. The compound of claim 30 wherein $R_3$ is selected from the group consisting of H, alkyl(1-6), and alkoxy.

6. The compound of claim 1 wherein $R_1$ and $R_2$ are the same and are selected from the group consisting of —C≡$CR_3$, —CH=$CHR_3$, and —CH=C=$CHR_3$.

7. A compound of the formula

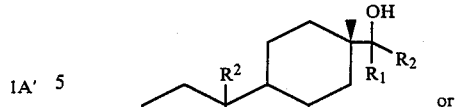

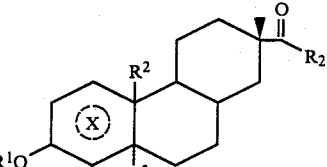

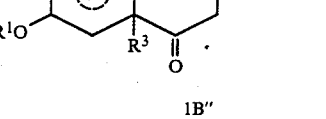

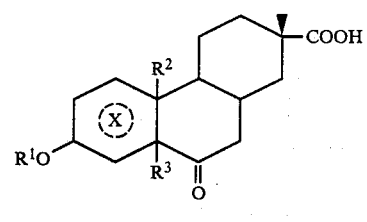

wherein (x) represents an aromatic ring or the presence or absence of 0, 1, or 2 conjugated or unconjugated π bond(s)
and wherein:
$R^1$ is H, acyl of (1-7), or alkyl of carbon atoms (1-6),
$R^2$ is H, alkyl(1-6), 2-propynyl, or allenyl;
$R^3$ is H or $OR^5$, wherein $R^5$ is H, acyl(1-6), or alkyl of (1-7) carbon atoms; and
wherein $R_1$ and $R_2$ is each independently H, alkyl of (1-6) carbon atoms or is —C≡$CR_3$, —CH=$CHR_3$, or —CH=C=$CHR_3$, wherein $R_3$ is selected from the group consisting of H, halo, $CR_3$, alkyl of (1-6) carbon atoms, acyloxy, carboxy, carboalkoxylate, alkoxy, or alkylthio.

8. A compound of the formula:

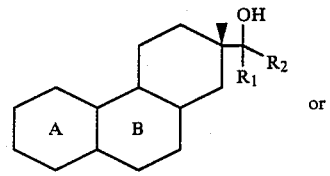

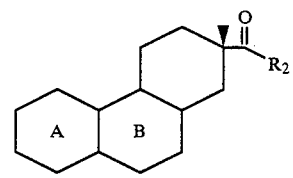

-continued

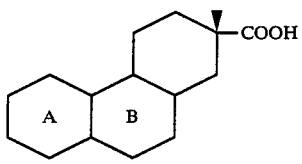

1C and the pharmaceutically acceptable esters thereof, wherein rings A and B are selected from the group consisting of

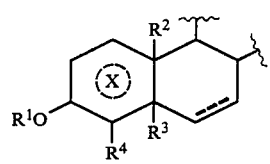

(a)

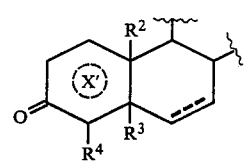

(b)

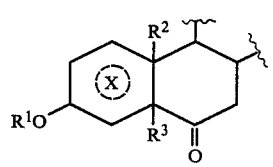

(c)

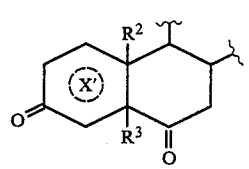

(d)

wherein $\textcircled{x}$ represents an aromatic ring, or the presence or absence of 0, 1, or 2 conjugated or unconjugated $\pi$ bond(s) and wherein x represents the presence or absence of 0, 1, or 2 conjugated or unconjugated $\pi$ bond(s) and and wherein the dotted line represents the presence or absence of a $\pi$ bond, and wherein:

$R^1$ is H, acyl of (1-7) carbon atoms, or alkyl of carbon atoms (1-6);

$R^2$ is 2-propynyl or allenyl;

$R^3$ and $R^4$ is each independently H or $OR^5$, wherein $R^5$ is H, acyl of (1-7) carbon atoms, or alkyl of (1-6) carbon atoms; and wherein $R_1$ and $R_2$ is each independently H, alkyl of (1-6) carbon atoms, or is —C≡$CR_3$, —CH=$CHR_3$, or —CH=C=$CHR_3$, wherein $R_2$ is selected from the group consisting of H, halo, $CR_3$, alkyl of carbon atoms (1-6), acyloxy, carboxy.

9. A compound of the formula:

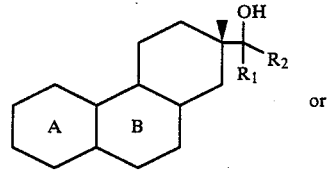

1A or

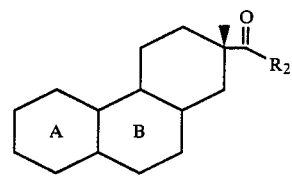

1B and the pharmaceutically acceptable esters thereof, wherein rings A and B are selected from the group consisting of (a)

(b)

(c)

(d)

wherein $\textcircled{x}$ represents an aromatic ring, or the presence or absence of 0, 1, or 2 conjugated or unconjugated bond(s) and wherein x' represents the presence or absence of 0, 1, or 2 conjugated or unconjugated $\pi$ bond(s)

and wherein the dotted line represents the presence or absence of a $\pi$ bond, and wherein:

$R^1$ is H, acyl of carbon atoms (1-7)), or alkyl of carbon atoms (1-6);

$R^2$ is H, alkyl(1-6), 2-propynyl, or allenyl;

$R^3$ and $R^4$ is each independently H or $OR^5$, wherein $R^5$ is H, acyl of (1-6) carbon atoms, or alkyl(1-6); and wherein $R_2$ is $-C{\equiv}CR_3$, $-CH{=}CHR_3$, or $-CH{=}C{=}CHR_3$, and $R_1$ is H, alkyl of carbon atoms (1-6), or is $-C{\equiv}CR_3$, $-CH{=}CHR_3$, or $-CH{=}C{=}CHR_3$, wherein $R_3$ is selected from the group consisting of H, halo, $CR_3$, alkyl of carbon atoms (1-6), acyloxy, carboxy, carboalkoxylate, alkoxy, or alkylthio, with the proviso that if $R_2$ is $-C{\equiv}CR_3$ or $-CH{=}CHR_3$ and $R_1$ is H or alkyl, $R_3$ cannot be H.

10. A compound of the formula

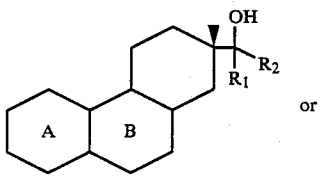

1A or

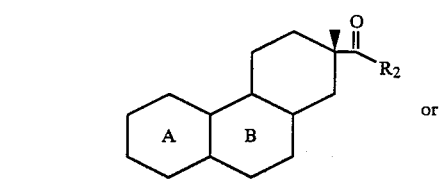

1B or

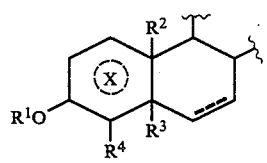

1C and the pharmaceutically acceptable esters thereof, wherein rings A and B are selected from the group consisting of

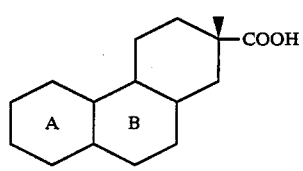

(a)

and

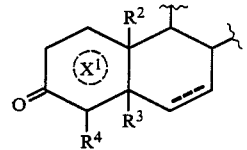

(b)

and wherein (x) represents an aromatic ring, or the presence or absence of 0, 1, or 2 conjugated or unconjugated ½ bond(s) and wherein (x) represents the presence or absence of 0, 1, or 2 conjugated or unconjugated π bond(s)

and wherein the dotted line represents the presence or absence of a π bond, and wherein:

$R^1$ is H, acyl of carbon atoms (1-7), or alkyl of carbon atoms (1-6);

$R^2$ is H, alkyl of carbon atoms (1-6), 2-propynyl, or allenyl;

$R^3$ is H or $OR^5$, wherein $R^5$ is H, acyl of carbon atoms (1-6), or alkyl of carbon atoms (1-6);

and $R^4$ is $OR^5$; and wherein $R_1$ and $R_2$ is each independently H, alkyl(1-6) or is $-C{\equiv}CR_3$, $-CH{=}CHR_3$, or $-CH{=}C{=}CHR_3$, wherein $R_3$ is selected from the group consisting of H, halo, $CR_3$, alkyl(1-6), acyloxy, carboxy, carboalkoxylate, alkoxy, or alkylthio.

11. A compound selected from the group consisting of:

[2S-(2α,4aα,10aβ)]-1-(1,2,3,4,4a,9,10,10a-octahydro-7-hydroxy-2-methyl-2-phenanthrenyl)-2-propyn-1-one,

[2S-(2α,4aα,10aβ)]-1,2,3,4,4a,9,10,10a-octahydro-7-hydroxy-α,α,2-trimethyl-2-phenanthrenemethanol,

[2S-(2α,4aα,10aβ)]-1,2,3,4,4a,9,10,10a-octahydro-7-methoxy-α,α,2-trimethyl-2-phenanthrenemethanol,

[2S-(2α,4aβ,4bβ,7β,8aα,10aβ)]-dodecahydro-2-hydroxy-α,α,-7-trimethyl-4a,10a-epoxyphenanthrene-7-methanol,

[2S-(2α,4aα,4bβ,7β,8aα,10aβ)]-tetradecahydro-2,10a-dihydroxy-α,α,7-trimethyl-4a-(2-propynyl)-7-phenanthrenemethanol, [4aS-(4aα,4bβ,7β,8aα,10aβ)]- dodecahydro-10a-hydroxy-7-(1-hydroxy-1-methylethyl)-7-methyl-4a-(2-propynyl)-2(1H)-phenanthrenone, and

[4aS-(4aα,4bβ,7β,8aα,10aβ)]-4,4a,4b,5,6,7,8,8a,9,10-decahydro-7-(1-hydroxy-1-methylethyl)-7-methyl-4a-(2-propynyl)-2(3H)-phenanthrenone.

* * * * *